US012797596B2

(12) United States Patent
Newton et al.

(10) Patent No.: US 12,797,596 B2
(45) Date of Patent: Nov. 17, 2026

(54) MEDICAL DEVICE CONTROL SYSTEM, CONNECTOR, MEDICAL CONTROLLER DEVICE ARRANGEMENT AND MEDICAL DEVICE ARRANGEMENT

(71) Applicant: Arjo IP Holding Aktiebolag, Malmö (SE)

(72) Inventors: Michael David Newton, San Antonio, TX (US); John Robert Hibberdine, Cardiff South Glamorgan (GB); Alaa Hassan, San Antonio, TX (US)

(73) Assignee: Arjo IP Holding Aktiebolag, Malmö (SE)

( * ) Notice: Subject to any disclaimer, the term of this patent is extended or adjusted under 35 U.S.C. 154(b) by 713 days.

(21) Appl. No.: 18/267,915

(22) PCT Filed: Dec. 15, 2021

(86) PCT No.: PCT/SE2021/051265
§ 371 (c)(1),
(2) Date: Jun. 16, 2023

(87) PCT Pub. No.: WO2022/132016
PCT Pub. Date: Jun. 23, 2022

(65) Prior Publication Data
US 2024/0307672 A1 Sep. 19, 2024

(30) Foreign Application Priority Data
Dec. 18, 2020 (SE) .................................... 2051492-3

(51) Int. Cl.
*A61M 39/10* (2006.01)

(52) U.S. Cl.
CPC ..... *A61M 39/10* (2013.01); *A61M 2039/1022* (2013.01); *A61M 2205/0227* (2013.01);
(Continued)

(58) Field of Classification Search
CPC .. A61M 2205/6054; A61M 2205/3592; A61M 39/10; A61M 39/1011; A61M 2039/1044
See application file for complete search history.

(56) References Cited

U.S. PATENT DOCUMENTS 6,884,255 B1 4/2005 Newton
7,398,803 B2 7/2008 Newton
(Continued)

FOREIGN PATENT DOCUMENTS

CN 1274409 A 11/2000
CN 102439602 A 5/2012
(Continued)

OTHER PUBLICATIONS

Office Action issued on Mar. 19, 2026 in Chinese Patent Application No. 202180091248.1.
(Continued)

*Primary Examiner* — Courtney Fredrickson
(74) *Attorney, Agent, or Firm* — Morgan, Lewis & Bockius LLP

(57) ABSTRACT

Present invention relates to a medical device control system (100) comprising a medical device (120) and a controller device (110) configured to control the operation of the medical device (120), the medical device control system (100) further comprising a coupling assembly (300) for connecting the medical device (120) and the controller device (110). The coupling assembly (300) comprises a connector (330) and a connecting member (310), the connector (330) being connectable to the connecting member (310) for forming a connection through said connector (330) and connecting member (310). The coupling assembly (300) comprises an identification device (390), said identification device (390) being adapted to generate a characteristic response associated with the controller device (110) or the medical device (120). The medical device control system
(Continued)

comprises a sensing arrangement (420) being configured to emit a sensing signal (S) in the form of a mixed radio frequency waveform by combining a carrier signal (C) and a mixing signal (M) for detecting the characteristic response.

13 Claims, 3 Drawing Sheets

(52) U.S. Cl.
CPC . *A61M 2205/0233* (2013.01); *A61M 2205/10* (2013.01); *A61M 2205/3327* (2013.01); *A61M 2205/3331* (2013.01); *A61M 2205/502* (2013.01); *A61M 2205/6036* (2013.01)

(56) References Cited

U.S. PATENT DOCUMENTS

| | | | |
|---|---|---|---|
| 8,587,410 B2 | 11/2013 | Potyrailo et al. | |
| 10,675,210 B2 | 6/2020 | Newton et al. | |
| 2004/0127937 A1* | 7/2004 | Newton | A61H 9/0078 606/202 |
| 2005/0033351 A1 | 2/2005 | Newton | |
| 2012/0001731 A1 | 1/2012 | Potyrailo et al. | |
| 2012/0229272 A1 | 9/2012 | Jacob et al. | |
| 2017/0105894 A1 | 4/2017 | Newton et al. | |

FOREIGN PATENT DOCUMENTS

| | | |
|---|---|---|
| CN | 106535855 A | 3/2017 |
| JP | 2002-521167 A | 7/2002 |
| JP | 2003-022428 A | 1/2003 |
| JP | 2007-199993 A | 8/2007 |
| JP | 2012-516494 A | 7/2012 |

OTHER PUBLICATIONS

Office Action issued on Mar. 17, 2026 in Japanese Patent Application No. 2023-537299.

International Search Report and Written Opinion issued in corresponding International Patent Application No. PCT/SE2021/051265, dated Mar. 22, 2022.

Office Action issued on Jul. 3, 2026 in Indian Patent Application No. 202317048226.

* cited by examiner

MEDICAL DEVICE CONTROL SYSTEM, CONNECTOR, MEDICAL CONTROLLER DEVICE ARRANGEMENT AND MEDICAL DEVICE ARRANGEMENT

TECHNICAL FIELD

The present invention relates to a medical device control system, a connector for a medical device control system, a medical device arrangement and a medical controller device arrangement.

BACKGROUND

This invention relates to medical device control systems such as pneumatic systems having a medical device connected to a controller device by means of a coupling assembly.

Current coupling assemblies often utilizes a type of 'quick-connect' or 'snap fit' two-part connector arrangement. This involves a purely mechanical engagement in order to provide the connection between the pump and the inflatable garment. In the case of the connection being a pneumatic connection, this can involve one or more separate air paths.

Many different connectors are available in this style and look very similar. It is therefore relatively easy for the user (or patient) to try to connect items that at first glance would appear to be compatible but which are not intended to operate together. As a result, there is a potential for a complication and hazard associated with the incorrect interconnection of these devices.

The relatively small physical size and shape of some of connectors commonly in use does not readily allow for extensive marking and physical features to aid the user to avoid misconnection, particularly those who may have vision limitations or limited dexterity such as those products designed for use in non-acute locations such as in a home-care environments. The use of color coding is also not fully effective for all users because of color vision deficiency (color blindness). The use of product marking techniques in general in itself also does not provide a failsafe operation as these can be ignored, inadvertently used/mis-used due to lack of understanding or coordination in the marketplace. The integration of a monitoring and identification process with the underlying operation of the product therefore provides a more effective solution than marking. Thus, there is a need for systems which mitigate the risks of such complications and hazards.

This may be performed by the article or the connector of the article being provided with a specific identification component, as described in for example U.S. Pat. Nos. 7,398,803 and 10,675,210.

The identification component present in the connector modifies the coil characteristics through a change in the coil inductance when the connector and identification component are located within the connector/coil. The modification being a function of the energization signal—such that different responses are achieved with different stimuli. The received modified response signal from the connector is analyzed by the pump, compared with the signal transmitted and processed using both electronic circuitry and software based processing elements. This allows the control device to categorize the attached medical device and hence allows for detection of the initial connection, sense its continued presence and configure the control device to operate the connected medical device in a safe and effective manner based on the type of medical device. This approach provides many advantages to the user compared to the products and systems that do not have this capability.

However, the systems described in the prior art (such as detailed in U.S. Pat. Nos. 6,884,255, 7,398,803 & 10,675,210) use a sensing signal that has a fixed frequency per component, the signal is periodic and does not change frequency, as such the sensing signal is either not present or is constant in terms of the frequency, type and amplitude. As a result of the fixed level of stimuli—the response is also a fixed response. Thus, the identification component present in the connector has a constant impact on the radio circuit used for this purpose. As a direct consequence, the resulting Electromagnetic Compatibility (EMC) performance of the sensing system can be considered as being broadly constant in nature, with a constant emission profile and also a constant degree of susceptibility to the effects of external interference.

In many fields of communication and device operation there is a need for robust and reliable communication to ensure safe and consistent operation and also to offer a lower noise method of operation to avoid interfering with other devices used in the same operational environment. Whilst there are various standards and measurements in place to limit radio emissions and ensure the inter-operability of equipment it is advantageous if the products are themselves able to operate in a highly robust manner and be able to be readily adapted to their operational environment.

For example, in the hospital operating room, there are many devices that either intentionally utilize levels of Radio Frequency (RF) energy as a basis for their intended function, such as electrosurgical generators or use RF for some other auxiliary function, such as remote communication or device tracking.

One area that that is becoming widely utilized is the RFID tagging and tracking of surgical devices, instruments, absorbent gauzes and other items near the patient to ensure that they are not inadvertently left in the patient during the surgical procedure.

These devices are often specifically fitted with RF location tags operating in this same 115 to 135 kHz range as other devices, such as compression systems. These tagged devices can be detected by a manual scanning wand that is passed over the patient at stages of the surgical procedure to ensure that all necessary RFID tagged devices have been removed. A further application involves the patient lying on a sensing mat with an embedded RFID detection coil to allow immediate detection of the presence of these tagged articles in proximity to the patient's body. This shares the operational environment as other devices utilizing the same frequency.

Outside of the operating room, Radio Frequency Identification Devices (RFID) are widely used for a wide range of devices from drug and device identifiers to patient bracelets for identity bracelets. It can therefore be readily seen that there is an increasing use of RFID within the healthcare facilities and the patient care environment itself. Since the applicants original work on compression garment identification was published (e.g. U.S. Pat. No. 6,884,255) the medical world has seen an unprecedented increase in the number of different devices that are in common usage. The use of RFID for asset tracking of devices has become routine and provides many benefits in terms of traceability, identification and product safety. As a result, the operation of future medical systems that are intended to intelligently and automatically operate together need to be even more tolerant to the wider EMC environment of the medical world. This is also particularly the case with increasing medical device inter-communication and inter-operation using wireless RF to interconnect.

The present invention seeks to modify this prior art approach so that that the operation is more robust and has minimum sensitivity to variations in uncontrollable factors such as external noise sources.

SUMMARY

According to an aspect, a connector for a coupling assembly for connecting a medical device and a controller device in a medical device control system is provided. The controller device is configured to control the operation of the medical device, the connector is connectable to a connecting member of the coupling assembly for forming a connection through said connector and connecting member.

The connector comprises an identification device, said identification device being adapted to generate a characteristic response associated with the controller device or the medical device. The characteristic response is detectable by means of being energized by a sensing arrangement of the medical device control system emitting a sensing signal in the form of a mixed radio frequency waveform by mixing a carrier signal and a mixing signal, wherein the characteristic response is between 80 kHz and 300 kHz.

According to an aspect, a medical device control system is provided. The medical device control system comprises a medical device and a controller device configured to control the operation of the medical device. The medical device control system further comprises a coupling assembly for connecting the medical device and the controller device.

The coupling assembly comprises a connector and a connecting member, the connector being connectable to the connecting member for forming a connection through said connector and connecting member.

The coupling assembly comprises an identification device, said identification device being adapted to generate a characteristic response associated with the controller device or the medical device.

The medical device control system further comprises a control unit and a sensing arrangement operatively connected to said control unit. The sensing arrangement is configured to emit a sensing signal in the form of a mixed radio frequency waveform by combining a carrier signal and a mixing signal for detecting a characteristic response associated with the medical device or the controller device.

Further objects and features of the present invention will appear from the following detailed description of embodiments of the invention.

BRIEF DESCRIPTION OF DRAWINGS

The invention will be described with reference to the accompanying drawings, in which.

DETAILED DESCRIPTION

Figure 1:
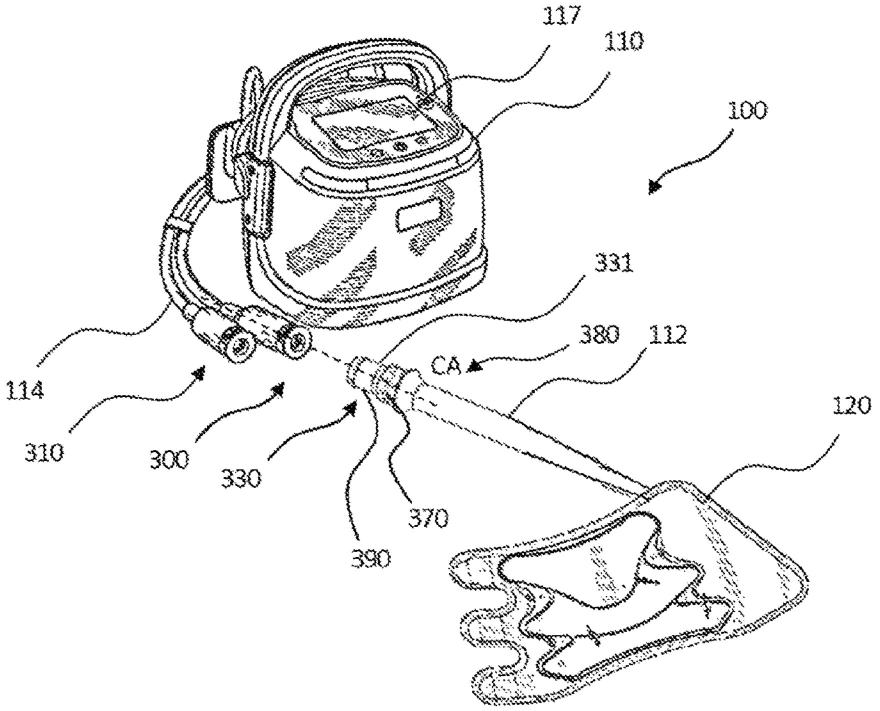
FIG. 1 depicts a medical device control system according to an embodiment of the present invention.

FIG. 1 depicts a medical device control system 100 wherein a connector 330, a medical device arrangement and/or a medical controller device arrangement according to the present invention may be implemented.

The medical device control system 100 comprises a medical device 120. The medical device control system 100 further comprises a controller device 110 for controlling the operation of the medical device 120. The controller device 110 may be configured to control the operation of the medical device 120.

The medical device control system 100 further comprises a coupling assembly 300 for connecting the medical device 120 and the controller device 120. The coupling assembly 300 comprises a connector 330 and a connecting member 310.

The connector 330 is connectable to the connecting member 310 for forming a connection through said connector 330 and connecting member 310.

The connector 330 may be connectable to the connecting member 310 to form various electrical connections, a fluid connection, an optical connection or combinations thereof. In one embodiment, the connector 330 is connectable to the connecting member 310 to form a plurality of an electrical, fluid or optical connection.

The medical device 120 may be any one of an inflatable/deflatable article, a measuring device and a disposable medical device.

In the embodiment shown in FIG. 1, the medical device 120 is an inflatable/deflatable article 120 and the controller device 110 is pump. Accordingly, the coupling assembly 300 forms a fluid connection between the inflatable article 120 and the controller device 110.

Accordingly, the medical device control system 100 may be a fluid pressure control system wherein a connector according to the present invention may be implemented. The fluid pressure control system 100 may be a gas pressure control system such as a pneumatic control system or may be based on any type of suitable fluid for the application with inflatable/deflatable articles.

The medical device control system 100 comprises the medical device 120 and a controlling device 110. The controlling device 110 is configured to control the operation of the medical device 120.

The controlling device 110 may comprise a control unit (not shown in FIG. 1). In one embodiment, the control unit is operatively connected to a pump of the controlling device 110 for controlling said pump.

In one embodiment, the pump may be a pneumatic pump. The pump may be arranged to control fluid flow to and from the inflatable/deflatable article. Accordingly, the pump may be arranged to inflate or deflate the inflatable/deflatable article.

The medical device control system 100 comprises the coupling assembly 300 for connecting the medical device 120 and the controlling device 110. The coupling assembly 300 comprises a connector 330 and a connecting member 310.

The connector 330 has a connector body 331. The connector body 331 is connectable to the connecting member 310 for forming a connection through the connector 330 and the connecting member 310. In one embodiment, the connector 330 and the connecting member 310 are connectable to form a fluid pathway through the connector 330.

The connection through the connector 330 and the connecting member 310 may be formed by means of insertion of the connector body 331 or a part of the connector body 331 into the connecting member 310. Thus, the connector body 331 may have a distal part 332 for coming into engagement with the connecting member 310.

The connector body 331 is movable inside the connecting member 310 along a connection axis CA. The connection axis CA extends distally from the connector 330, The distal part 332 is movable inside the connecting member 310 along the connection axis CA. Preferably, the distal part 332 and the connecting member 310 are adapted to sealingly engage when the connector body 331 is in a coupled position.

The connector body 331 may be movable from a non-inserted position to a non-coupled position. In the non-coupled position, the connector body 331 may have at least come into close proximity to the connecting member 310. In one embodiment, the connector body 331 may have at least come into contact with the connecting member 310 in the non-coupled position. A non-coupled position herein refers to a position of the connector body 331 inside the connecting member 310 wherein the coupling assembly does not provide a connection through the connecting member 310 and the connector 330. Correspondingly, a coupled position herein refers to a position of the connector body 331 inside the connecting member 310 wherein a connection through the connecting member 310 and the connector 330 is achieved.

In one embodiment, substantially the entire length of the distal part 332 may be inserted into the connecting member 310 when the connector body 331 is in the coupled position.

Further referencing FIG. 1, the medical device control system 100 comprises a medical device connection 112. The medical device 120 may be connected to the connector 330 by means of said medical device connection 112.

Thus, a medical device control system 100 may comprise the medical device 120, the medical device connection 112 and the connector 330. The medical device 120 being connected to the connector 330 by means of the medical device connection 112.

The medical device control system 100 may comprise a controller device connection 114. The controller device 110 may be connected to the connecting member 310 by means of said controller device connection 114.

In one embodiment, wherein the medical device control system is a fluid pressure control system, the connector 330 may be fluidly connected to the medical device 120 by means of a device fluid connection (i.e. medical device connection 112). The article fluid connection may be a tube or a hose. Correspondingly, the connecting member 310 may be fluidly connected to the controller device by means of a controller device fluid connection (i.e. controller device connection 114). The controller device fluid connection 114 may be a tube or a hose.

To allow for identification of the medical device or the controller device, the medical device control system 100 may further comprise an identification device 390. The identification device 390 is adapted to generate a characteristic response associated with the controller device 110 or the medical device 120.

Figure 3:
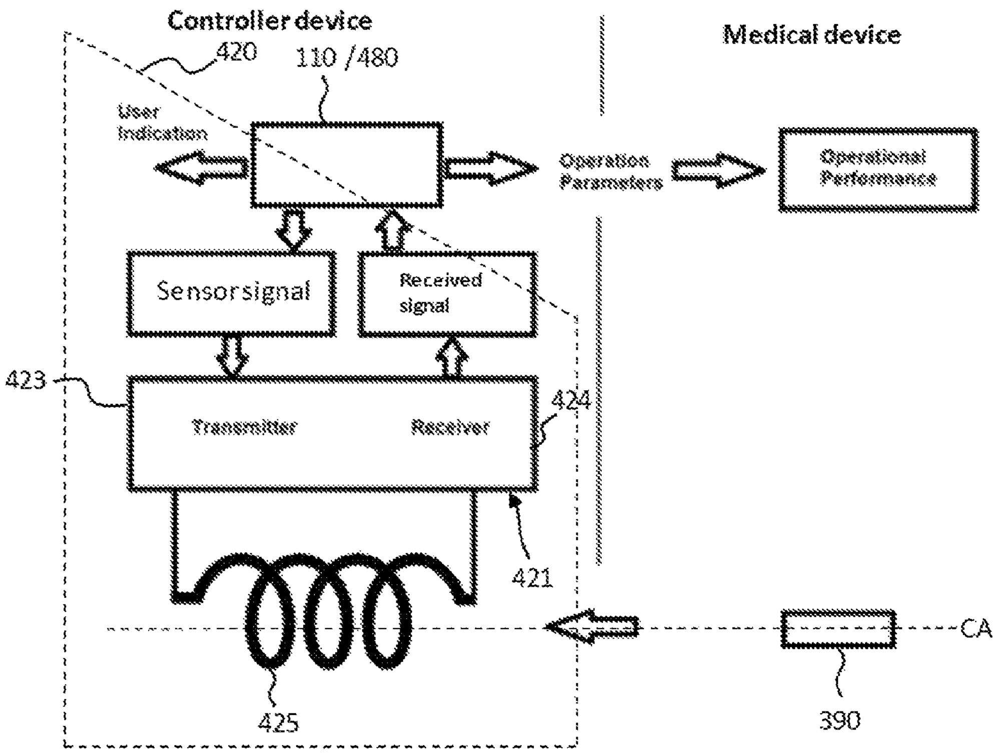
FIG. 3 depicts a schematic system diagram of a medical device control system according to an embodiment of the present invention.

Further, the medical device control system 100 may comprise a control unit 480 and a sensing arrangement 420 (introduced in FIG. 3). The sensing arrangement 420 is operatively connected to the control unit 480.

The coupling assembly 300 may thus comprise an identification device 390. As will be further described with reference to FIG. 3, the sensing arrangement 420 may be configured to emit a mixed radio frequency waveform for detecting a characteristic response associated with the medical device 120 or the controller device 110.

Further, the controller may be configured to compare the characteristic response generated by the identification device 390 with a set of stored characteristic responses associated with a corresponding set of medical devices or controller devices to identify the medical device 120 or the controller device 110.

In one embodiment, the sensing arrangement 420 may be configured to emit at least one mixed radio frequency waveform, a sensing signal, for detecting at least one characteristic response associated with the medical device 120 or the controller device 110. The mixed radio frequency waveform may comprise at least one carrier frequency or may comprise multiple carrier frequencies sequentially selected by the transmit mixer 427.

Further, the controller may be configured to compare the at least one characteristic response generated by the identification device 390 with a set of stored characteristic responses associated with a corresponding set of medical devices or controller devices to identify the medical device 120 or the controller device 110.

In one embodiment, the control unit 480 is comprised in the controller device 110. The control unit 480 may be configured to control the controller device 110 based on the characteristic response generated by the identification device 390.

In one embodiment, the control unit 480 may be separate to the controller device 110. Thus, the control unit 480 may be an external control unit operatively connected to the sensing arrangement 420 and the controller device 110. In a further embodiment, the control unit 480 is comprised in the sensing arrangement 420.

The control unit 480 may be configured to compare the characteristic response with a set of stored characteristic responses. The set of stored characteristic responses are associated with a corresponding set of controller devices 110 or medical devices 120 to identify and confirm the compatibility of medical device and controller device.

The set of stored characteristic responses may be stored in a memory of the control unit 480.

The medical control device control system 100 may comprise an indicating device 117. The indicating device is operatively connected to the controller 480. In one embodiment, the indicating device 117 is configured to provide an indication to a user based on the characteristic response generated by the identification device 390.

Referencing FIG. 1, the indicating device 117 may be provided on the controller device 110. In one embodiment, the indicating device 117 may be a display device such as an LED or LCD display. In one embodiment, the indicating device 117 may be any one of a speaker, light or tactile indicating device. A tactile indicating device may be configured to selectively vibrate to provide an indication to a user. Such a tactile indicating device may for example be provided on the connecting member 310 or the connector 330. The tactile indicating device may be a selectively oscillating element operatively connected to the control unit.

In one embodiment, the connector 330 comprises the identification device 390. The identification device 390 being adapted to generate the characteristic response associated with the controller device 110 or the medical device 120. The characteristic response is detectably by means of being energized by the sensing arrangement 420 of the medical device control system 100 emitting a mixed radio frequency waveform. The identification device 390 may be adapted to generate the characteristic response in a range between 80 kHz and 300 kHz. This is beneficial since relevant designs are typically focused, i.e. intentionally tuned, around 115-125 kHz which is the frequency band of RFID. A tolerance is added to this frequency range in order to align with a number of ISM bands where there is wide use of differing items of equipment. Further to this, allowing for Fourier effects provides a wider range on the top tolerance, this is one benefit from extending it to 300 kHz i.e. more than 2 times the nominal top frequency. Further extensions, i.e. past 450 kHz, introduces noisier areas, e.g. areas reserved for devices such as electrosurgical generators/ diathermy. Thus, a compatibility functionality is achieved in a manner which is less susceptible for external noise and hence more robust during operation.

The characteristic response may be a combination of the applied waveform and the identification device. As a result, a number of individual characteristic responses can be generated for a given identification device in an attached medical device 120 through the modification of the applied waveform, As aforementioned, the connector 330 may be connectable to the connecting member 310 to form any one of or a plurality of an electrical, fluid or optical connection.

The connector 330 may be connectable to the connecting member 310 to form a fluid connection for connecting a medical device in the form of an inflatable garment pump and a controller device in the form of a pump in a medical device control system in the form of a medical fluid pressure control system.

A first characteristic response is generated and associated with the location of the connector when the distal part 331 is not located in the coupled position but is instead located in the uncoupled position.

A second characteristic response is generated and associated with the location of the connector when the distal part 331 is located in the coupled position.

According to an embodiment, the coupling assembly 300 may further comprise a mechanical latch 370. The mechanical latch 370 is arranged to secure the distal part 331 is in the coupled position. The coupled position may thus be a latched position of the distal part.

The mechanical latch 370 may be a manually operated mechanical latch adapted to be engaged by a user to secure the connector body 331 when said connector body 321 is in the coupled position, i.e. is in engagement with the connecting member 310.

Alternatively, the mechanical latch 370 is adapted to resiliently engage to secure the connector body 331 when said connector body 331 is in the coupled position.

Preferably, the mechanical latch 370 comprises a locking member provided on the connecting member 310 or the connector 330 and a retention member provided on the other of the connecting member 310 or the connector 330. When the connector body 331 is in the coupled position, the retention member is arranged to engage the retention member, whereby the mechanical latch 370 is secured relative the connecting member 310.

Mechanical latches are well-known in the prior art and will not be described in further detail.

Figure 2:
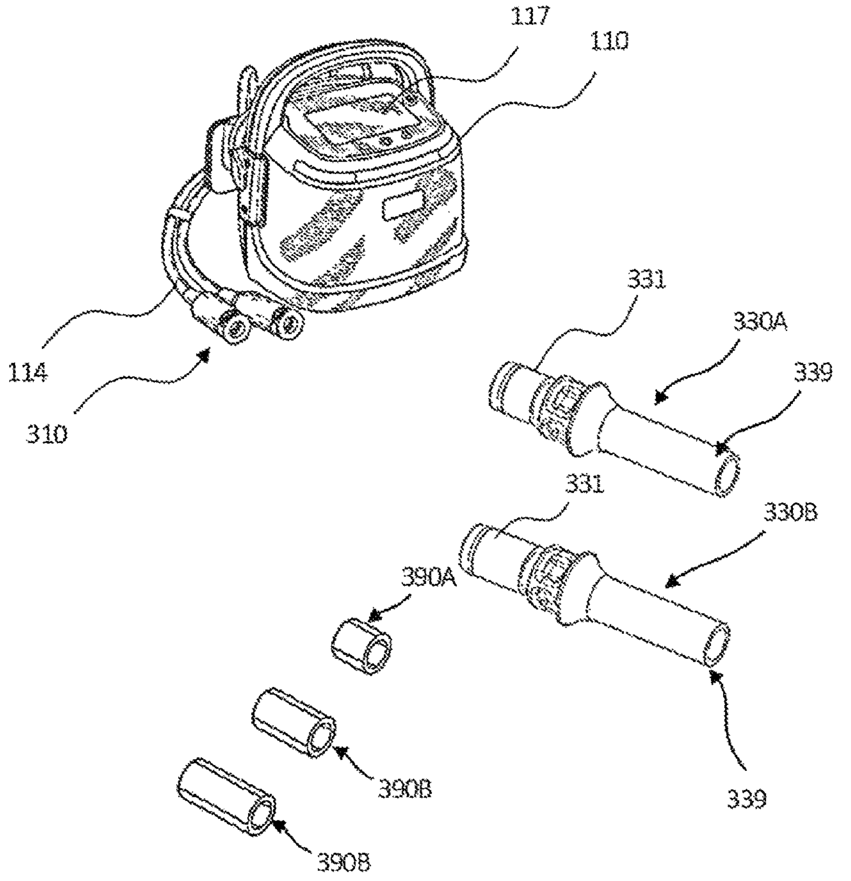
FIG. 2 depicts a medical device control system and various identification devices according to an embodiment of the present invention.

Turning to FIG. 2 different types of identification devices 390A, 390B, 390C in conjunction with a medical device control system 100 are depicted.

In one embodiment, the sensing arrangement 420 may be provided on the connecting member 310 and/or the controller device 110 and the identification device 390 may be provided on the connector 330.

Accordingly, the sensing arrangement 420 may be configured to detect a characteristic response associated with the medical device 120.

According to an embodiment, the identification device 390 may be provided on the distal part 331 of the connector 330. Preferably, the identification device 390 may have a length extending along the connection axis CA of more than 2 mm. In order to allow for differentiating between different types of components of the fluid pressure control system, the size, material characteristics and shape of identification device 390 may vary.

In one embodiment, the identification device 390 is made of any one of a ferrite material, brass material and a ferromagnetic material.

In one embodiment, the identification device 390 is substantially cylindrical.

In one embodiment, the identification device 390 has a length extending along the connector 330 of at least 2 mm.

Advantageously, the characteristic response generated by the identification device 390 varies in response to variations in the mixed radio frequency waveform. In one embodiment, the characteristic response generated by the identification device 390 varies in response to the individual frequency components and variations in the mixed radio frequency waveform.

As depicted in FIG. 2, the identification device 390 may have a generally cylindrical or toroidal shape. Advantageously, the identification device 390 has an outer dimension (i.e. maximum width or height orthogonal to the connection axis) of between and 10 mm and preferably between 6 and 8 mm. The identification device 390 may have an inner dimension (i.e. an inner diameter) of preferably less than 6 mm and more preferably greater than 4 mm. The identification device 390 may have a length extending along the connection axis of between 1 and 10 mm and more preferably between 2 and 9 mm.

In one embodiment, the connector 330 may comprise a data storage device. The data storage device may carry data associated with the medical device 120 or the controller device 110. The data storage device may thus operate independently from the identification device to allow for indication of a medical device or a controller device. In one embodiment, the identification device in itself may be a data storage device according to the aforementioned.

In one embodiment, the identification device 390 may be operated with either a separate data storage device or be itself in the form of a data-storage device. For example, the data storage device may be an active or passive tag comprising a readable and/or writable digital memory e.g. a passive RFID-tag. The data storage device may be configured separately from the identification device 390 such that data readable from the digital memory may be used e.g. in speeding up the detection of the identification device 390. Alternatively or additionally, the combination of the identification device 390 and the data storage device may allow additional functionality or security e.g. for a two step verification process wherein the identification device 390 is read in order to acquire a key that is then used to decode information stored on the data storage device. Advantageously, the same reading and sensing techniques and methods can be used to communicate with either the identification device or the data storage device. The data storage device can also be used for a variety of purposes apart from identification, for example recording usage data of the connected device.

In one embodiment, the identification device 390 may be an impedance element having a frequency dependent impedance associated with the controller device 110 or the medical device 120.

A number of further alternative embodiments of identification devices 390 exist that are within the scope of the invention and should be obvious to anyone skilled in the art of position sensing and object detection.

The identification device may be configured to generate at least one characteristic response while the distal part 331 is inserted into the connecting member 310, i.e. when within the sensing arrangements operational range. Said characteristic responses may be detectable by means of the sensing arrangement 420.

In one embodiment, the identification device may be configured to generate at least one characteristic response while the distal part 331 is inserted into the connecting member 310, i.e. when within the sensing arrangements operational range.

The operational range of the sensing arrangement 420 being between 10 mm to 50 mn distance along the connection axis CA from the coupled position.

Further referencing FIG. 2, the connector 330 may comprise a connector body 331 with a barrel 339. Said barrel 339 may be connectable to the connecting member 310 to form the connection.

The identification device 390 may be arranged inside the barrel 339. Thus, the identification device 390 is less susceptible for tampering, wear and damage.

FIG. 3 depicts a schematic figure of the medical device control system 100 and the insertion of the distal part 331 into the connecting member 330.

In the embodiment depicted in FIG. 3, the identification device 390 is provided on the connector and more specifically the distal part 331. The sensing arrangement 320 comprises at least one sensor unit 421.

In one embodiment, the sensor unit 421 may be provided on the connecting member 310. In one embodiment, the sensor unit 421 may be arranged externally from the connecting member 310.

Thus, the sensor unit 421 may be provided distally to the controller such as on the connecting member or alternatively may be located more proximally such as on the body (casing) of the controller device 110.

Preferably, the sensor unit 421 is arranged externally from the connecting member 310, this allows for mounting of the sensor unit 421 to the controller device 110. Thereby, the electronics of the system may be kept together on a single PCB which is advantageous both from a cost and complexity standpoint. Further, this allows for a connecting member without costly electronic components which makes it easier and cheaper to replace.

As will be described in further detail below, the sensing arrangement as a whole may be arranged on both the controller device and connecting member.

The use of non-contact as a basis for sensing is particularly advantageous as it avoids a number of issues associated with potential alternative embodiments that use a physical contact means such as problems associated with the buildup of debris/material on contacts, regulatory concerns regarding exposed electrical contacts and physical damage to the alignment of a contact.

Referencing FIG. 3, the sensor unit 421 may comprise a transmitter 423 and a receiver 424. The transmitter 423 is configured to generate a sensing signal. The sensing signal is received by the receiver 424. The position signal is based on the characteristics of the signal received by said receiver 424. The signal received by the receiver 424 may be considered the measured value obtained by the sensing arrangement.

Thus, the sensor unit 421 comprises the transmitter 423 and the receiver 424, said transmitter 423 being configured to emit the mixed radio frequency waveform to the receiver 424 for forming a sensor field between said transmitter 423 and receiver 424.

With reference to FIG. 3, the sensing arrangement may be an induction based sensing arrangement. Thus, the sensor arrangement 420 may be an induction sensor. Preferably, the sensing arrangement 420 may be a radio-based sensing arrangement 420, preferably the radio system operating primarily in the frequency band 80 kHz to 300 kHz Further referencing FIG. 3, the sensing arrangement 420 may further comprise a sensor coil 425. The sensor coil may be configured to couple the transmitter 423 and the receiver 424.

The sensor coil 425 may be operatively connected to the transmitter 423 and the receiver 424. In one embodiment, the sensor coil 425 may be arranged to be coaxial to the connection axis CA.

Said sensor coil 425 may be configured to generate an electromagnetic field extending along the connection axis CA, whereby the identification device 390 is detectable inside said electromagnetic field. The identification device 390 causes a change in the received signal compared to the sensing signal indicative of the position and/or movement of the identification device inside said electromagnetic field.

Accordingly, the configuration of the sensor coil 425 may be chosen such that the electromagnetic field extends along said connection axis CA.

Preferably, the sensor coil 425 is provided on the connecting member 310. In one embodiment, the sensor coil 425 may be provided inside the connecting member 310.

Having the sensor coil 425 provided on the connecting member 310 allows for easy service and potential replacement of the coil.

In an alternative embodiment, the sensor coil 425 may be provided in the controller device connection 114.

The identification device 390 may preferably be made of a material selected from a group consisting of a ferrite material, steel and a brass material. The identification device 390 may be fitted to the distal part of the connector 300. For example, the identification device may be a ferrite ring, in a toroidal format. Other materials can provide a similar effect such as certain grades of steel and brass.

The material (for example ferrite) in the identification device 390 forms a variable permeability core to the sensor coil 425. Thereby, the coil inductance is modified. This change in inductance can be detected by means of electrical circuitry in the controller 480 as a phase change in the sensor coil current resulting from the applied waveform signal and also as an amplitude change to the current flowing in the sensor coil 425. According to the embodiment depicted in FIG. 3, the sensor coil 425 may be provided on the connecting member which may be associated with the pump.

In one embodiment, a single coil may be used to transfer the sensing signal between the transmitter and receiver. Accordingly, the transmitter 423 and receiver 424 may be in electrical connection with the sensor coil 425. The electrical connection is, in preferred embodiments, arranged such that the transmitter 423 and receiver 424 are in electrical conductive connection through the sensor coil 425. In one embodiment, the sensor coil 425 may be mounted in the connecting member. In one embodiment, may be mounted in the casing of the pump.

Other embodiments within the scope of the invention include the use of a split coil with independent connections/windings where the transmit and receive signals are separate. Thus the sensing arrangement 420 may comprise a receiver coil and a transmitter coil, whereby the received signal is separate from the sensing signal, i.e. the signal transmitted from the transmitter coil.

Alternatively, it is also possible to use separate transmit and receive coil arrangements where the two coils are always used for different purposes.

In one embodiment, the sensor coil 425 is arranged to allow for fluid flow through a central axis of said sensor coil 425. The central axis of the sensor coil 425 may be substantially aligned with the connection axis CA.

In one embodiment, the sensor coil 425 may be in the form of a 'Brooks coil', i.e. it being dimensioned according to the well established 'Brooks coil' relative dimensions to allow for manufacturing efficiencies in coil winding and maximizing the resulting inductance provided by the wire used in the coil. This dimensional requirement is extended such that the sensor coil 425 may have a length of 5 mm in the direction of the connection axis CA. This allows ensures that the majority of the resulting electromagnetic field can be utilized by the identification device during the connector insertion process.

The aforementioned coil dimensioning helps to optimize operation in use, improve coupling and reduces the physical size requirements whilst ensuring maximum coil sensitivity to the introduced identification device material.

This optimal dimensioning involves ensuring the ratio of the inner diameter of the sensor coil 425, (which may form the path for the distal part of the connector and therefore the fluid flow), to the coil length being at least 2 and preferably the ratio of sensor coil 425 outer diameter to identification device length being at least 5.

In one embodiment, the sensor coil 425 has an inductance of 400-500 uH, preferably 446 uH when no identification device 390 is present in or at the coil.

Figure 4:
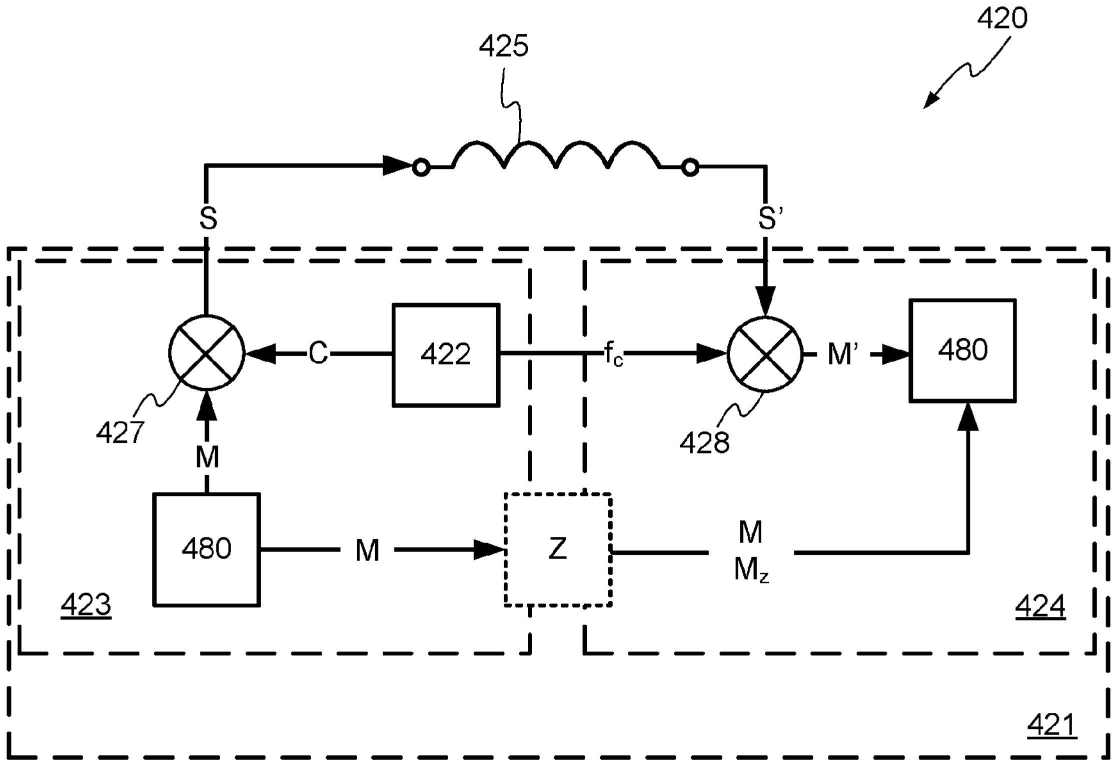
FIG. 4 depicts a schematic view of a sensing arrangement according to an embodiment of the present invention.

With reference to FIG. 4, the sensing arrangement 420 according to one embodiment will be explained. As mentioned earlier, the transmitter 423 of the sensing arrangement 420 is configured to generate and transmit a sensing signal S. The sensing signal S is generated by the transmitter 423 and is a mixed radio frequency waveform at a carrier frequency fc modulated with a mixing signal M. The transmitter comprises a transmit mixer 427 configured to generate the sensing signal S by mixing a carrier signal C at the carrier frequency fc with the mixing signal M. The transmitter 423 further comprise a frequency generator 422 configured to generate the carrier signal C. The mixing signal M is generated by a modulator module in the control unit 480, in this embodiment comprised in the sensor unit 421, but may very well distally located to the sensor unit 421. The mixing signal M may very well be generated by any suitable circuitry or software as will be understood by the skilled person after digestion of the teachings of this disclosure. The mixing signal may be a signal modulated at a modulation frequency $f_m$. The modulation frequency $f_m$ may be chosen arbitrarily but high modulation frequencies $f_m$ will typically put constraints on the speed and sensitivity of the receiver 424 of the sensor unit 421. Analogously, low modulation frequencies $f_m$ will make it easier to process the mixing signal M in the receiver, but the time it takes to detect what controller device 110 or medical device 120 is sensed will increased. These trade-offs are well understood by the skilled person and will, after digestion of this disclosure, not hinder said skilled person from implementing the invention as taught herein.

An output of the transmit mixer 427 is operatively connected to an input port of the sensor coil 425 such that the sensing signal S may be provided to the input port of the sensor coil 425. An output port of the sensor coil 425 is operatively connected the receiver 424 and input to a receive mixer 428 comprised in the receiver 424. It should be noted that the connection from either mixer 427, 428 to the sensor coil 425 may very well comprise additional circuitry and components e.g. filters, impedance matching elements, amplification circuitry etc.

As the sensing signal S is passed from the input port of the sensor coil 425 to the output port of the sensor coil 425, the sensing signal S is affected by the sensor coil 425 and a sensor response signal S' is proved at the output of the sensor coil 425. The receiver mixer 428 mixes the sensor response signal S' with the carrier signal C to provide a mixing response signal M'. The mixing response signal M' is provided to the detector module of the control unit 480, typically via an analogue to digital, A/D, converter. The control unit 480 analyzes the mixing response signal M' in order to identify the characteristic response of the controller device 110 or the medical device 120, this will be further explained in coming sections.

It should be mentioned that the receiver 424 may be implemented substantially in software, wherein the output of the sensor coil 425 is operatively connected to an A/D converter or equivalent circuit. A digital output form this A/D converter may be subjected to signal processing according to teaching known in the art in order to produce the mixing response signal M'.

The sensing signal S is a signal that can be described as a function of time, s(t), and subjecting this sensing signal S to a coil transfer function h(t) of the sensor coil 425 will produce the sensor response signal S' according to the equation below:

$$s'(t) = s(t) * h(t)$$

The coil transfer function h(t) will be affected by the presence of the identification device 390 such that different coil transfer functions $h_0(t)$, $h_1(t)$ . . . $h_n(t)$ will be provided by the sensor coil 425 depending on its proximity to and the type of the identification device 390. As a result, it should be clear that the multiple sensor response signals S' available will allow for both the position of the identification device 390 and its type to be readily ascertained during both the dynamic and static motion aspects of the insertion and coupling together of the various connector elements. If the sensing signal S was the carrier signal C directly, without any mixing signal M, the ability to differentiate different coil transfer functions $h_0(t)$, $h_1(t)$ . . . $h_n(t)$ from each other would be limited due to constraints with regards to e.g. processing speed and noise in the detector module. In system engineering terminology, the resulting arrangement forms a linear time-invariant system where the system response is dependent on three independent factors, applied stimulus signal to the sensor coil 425, identification component type, i.e. the identification device 390, and identification position relative to the sensor coil 425. The operation of the control unit 480 is configured to be able to identify the type of identification device 390 and position factors through the use of different sensing signals S, i.e. stimulus signals, applied at multiple times.

The detector module will analyze the mixing response signal M', or the sensor response signal S' directly depending on configuration, in order to identify a current coil transfer function h(t). The detector module may be configured to perform this analysis in a number of different ways. In a preferred embodiment, the mixing response signal M' is compared to the applied mixing signal M to see how they differ, the difference will be associated the coil transfer function h(t). The output from the detector module is a signal or message making it possible to determine the controller device 110 or the medical device 120, if any, sensed by the sensing arrangement 420. Typically, this determination is provided by the control unit 480 comparing the characteristic response of the sensor coil 425, i.e. the current coil transfer function h(t) to one or more predefined characteristic responses associated with different controller devices 110 and/or medical devices 120 in order to determine what controller device 110 or medical device 120 is sensed.

In some embodiments, the modulation module is configured to generate a predefined mixing signal M. In such embodiments, it is straight forward for the detector module to detect the current coil transfer function h(t) since the mixing signal M is known.

In some embodiments, the modulation module is configured to generate a random, or pseudo random mixing signal M. In such embodiments, the mixing signal M is typically provided to the detector module, optionally via a delay element Z, such that the detector module has knowledge of what mixing signal M the carrier signal C is modulated with. In some embodiments, the pseudo random mixing signal M is generated using a 127 bit Pseudo Random Bit pattern Sequence, PBRBS, such as a PRBS7 bit pattern commonly defined as $x^7+x^6+1$.

As already mentioned, there are many benefits of modulating the carrier signal C by a mixing signal M. The mixing will at least increase the bandwidth of a power of sensing signal S is transmitted resulting in a distribution of the power the sensing signal S. This will reduce the potential for the sensing arrangement 420 disturbing other equipment and also help to meet some of the various requirements placed upon the medical device 120 and its components, e.g. EMC and EMI, and ensure that they are more effectively met. The sensitivity of the detection is increased in terms of the mixed sensing signal S. Due to the increased sensitivity of operation, it may be possible to decrease the transmitted power of the sensing signal S thus further reducing any interference and also presenting an opportunity to save on power consumption in the sensing arrangement 420. A further benefit of the increased sensitivity during operation ensures that an increased resolution of measurement of types of identification components 390 is possible.

Figure 5:
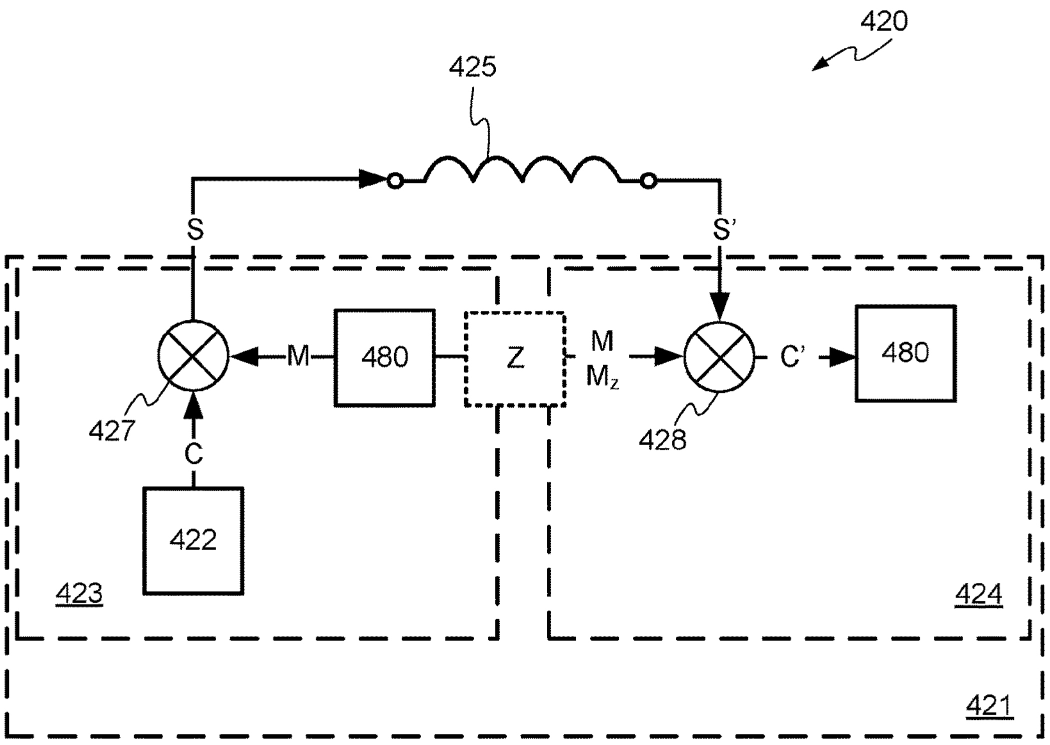
FIG. 5 depicts a schematic view of a sensing arrangement according to an embodiment of the present invention.

Turning to FIG. 5, one preferred embodiment of the sensing arrangement 420 will be presented in order to explain the spread spectrum capabilities of the sensing arrangement 420. The sensing arrangement 420 is similar to the sensing arrangement 420 of FIG. 4 and they may very well be the same sensing arrangements 420. The sensing arrangement 420 explained with reference to FIG. 4 utilized the receiver 424 to detect the mixing response signal M'. The sensing arrangement 420 of FIG. 5 is configured to detect the carrier signal C. Assuming that the carrier signal C is a constant carrier signal C at a carrier frequency fc, the mixing characteristics of the transmit mixer 427 will utilize the carrier signal C to generate a sensing signal S comprising a number of different frequencies. Each of these frequencies will be affected differently by the sensor coil 425 and the identification device 390. By mixing the sensor response signal S' with the mixing signal M, or a delayed mixing signal $M_z$, a carrier response signal S' may be provided to the control unit 48.

Figure 6A:
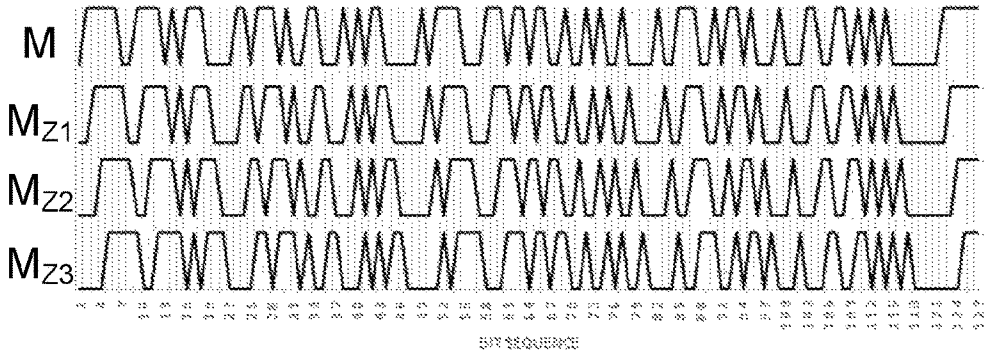
FIG. 6*a-b* depicts graphs of signals of the sensing arrangement according to an embodiment of the present invention.
Figure 6B:
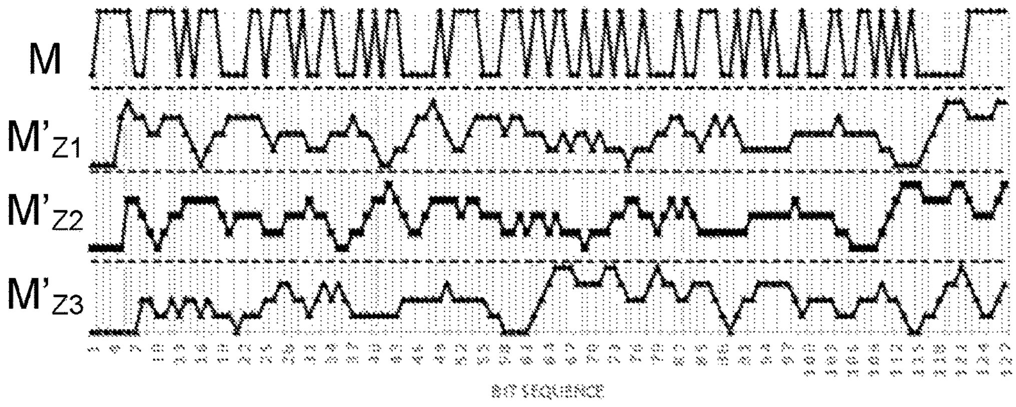

In further embodiments of the sensor arrangement 420 of FIG. 5, the detector module is configured to utilize autocorrelation functions in order to determine one or more mixing response signals M' from the sensor coil 425 and how it/they have been affected by any identification component 390. Turning briefly to FIG. 6*a*, one example of a mixing signal M is shown together with three delayed mixing signals $M_{Z1\text{-}3}$ that are delayed a number of bits compared to the mixing signal M. By comparing the mixing response signal M' with the mixing signal M and also the delayed version of the mixing signal $M_{Z1\text{-}3}$ yet further sensing possibilities and improvements are possible. This is due to the relationships between the applied signal, the time response of the electrical components and the autocorrelation function. Autocorrelation of the delayed version of the mixing signal $M_{Z1\text{-}3}$ will result in corresponding delayed mixing signal response signals $M'_{Z1\text{-}3}$. These are shown in FIG. 6*b* and, as the skilled person will understand, they will differ depending on the applied mixing signal M. Consequently, autocorrelation will allow for more than one mixing response signal M' to be generated from one sensing response signal S', this will greatly increase the sensitivity of the sensing arrangement 420. The resulting increase in the sensing methods available allows for improvements both in the signal to noise ratio of operation, increased dynamic range and hence more sensitive operation as well as operation at lower coil current resulting in lower RF power levels. This allows for an advantageous reduction in the overall RF emitted power of the output, for example the techniques employed allow have shown to allow operation at least a −3 dB reduction in operating power, i.e. 50% reduction. This benefit also applies to the operation of the mixing response signal M' detected during different aspects of the connector engagement, monitoring and use. This covers aspects from initial insertion, through partial and full engagement of the connector and identification component located in the garment connector through to the reverse situations during the removal process.

These advantages allow for increase in the number of discrete devices that can be uniquely sensed compared to the techniques described in the prior art. These techniques can be used to increase the sensitivity of measurement of the identification component as well as increase the robustness when there is interference from other sources by increase the noise immunity of the system in the operating environment. The carrier response signal S' may, depending on the mixing signal M, and if transformed into the frequency domain, be described as representing a frequency response of the sensor coil 425 or a frequency response of the sensor coil 425 and the identification device 390 if this is proximal to the sensor coil 425. The response being able to be characterized by the medical device control system 100 as a means of identifying the specific type of identification component 390 present from a plurality of different identification components 390. The accuracy and detail of the frequency response will depend on the number of frequencies the sensing signal S is spread across. Ideally, the sensing signal S is distributed within the relevant bandwidth, in the form of white noise, i.e. more evenly spread across the relevant bandwidth than would otherwise be the case with a single carrier frequency. Relevant bandwidth is herein defined to mean bandwidth equal to or in the vicinity of a bandwidth of the receiver 424. This can be simulated by providing the mixing signal M as a PRBS stimuli as described above at a modulation frequency $f_m$ that is lower than the carrier frequency fc such that modulation products are evenly spread across the relevant bandwidth.

Having the sensing signal S spread across a relevant bandwidth will make it possible to more accurately differentiate one identification device 390 from a large number of identification devices simply by having the receiver 424 measure a signal power within the relevant bandwidth. Since different identification devices 390 will have different frequency responses, the total effective attenuation, or amplification, they will have in the sensor coil 425 will differ. Consequently, a simple signal power detection may suffice in determining what controller device 110 or medical device 120 is sensed.

In other words, the application of a complex impulse, the sensing signal S, in the form of e.g. a PRBS-modulated pulse to the sensor coil 425 thereby results in a complex impulse response, the sensor response signal S', that can be measured and used for identification and device categorization purposes. The modulation signal M is used to change the characteristics of the transmitted carrier waveform, the sensing signal S, as well as being used to decode the received signal, the sensor response signal S'. Through the use of repeated operations of the sensing system, the position of the identification component relative to the coil can be determined. This invention therefore combines the field of medical device control systems and communications with various established approaches in the field of electronic communications and aspects of signal processing known generically as Spread Spectrum techniques. The modulation can be applied in a manner such that the PRBS operates at a higher frequency than the carrier frequency fc or alternatively it can be applied at a lower frequency to the carrier frequency fc as described herein, both techniques are within the scope of the invention. It should be clear to anyone skilled in the art, after reading this disclosure, that many further other alternative modulation approaches can be used and so also form part of the invention scope. Many coding or mixing waveforms are available for use in this application that have different repetition, lengths and characteristics that result in differing spectral characteristics when used for this modulation purpose and these are within the scope of the invention. Specifically sequential code sequences that have a maximal length property (e.g. Pseudo Random Binary Sequences) are included in the scope of the invention since they provide the necessary beneficial spectrally flatter characteristics. Other specific examples of waveform encoding that are also within the scope of the invention include Barker sequences, Gold codes, Kasami sequences, Complementary sequences and Golay codes. These are included in the scope of the invention since they also provide beneficially flat or complementary spectral characteristics as well as having differing degrees of signal cross-correlation that can be used to reduce the interference with other similar devices. The use of these type of sequences also allows a means for the control unit 480 to readily detect noise from other equipment though a de-synchronization method and hence automatic modify its own operation to a different timing or frequency where the ambient noise level is less. As a result, the sensing arrangement 420 can automatically adapt its operation to the EMC situation that it finds itself in its installed operating environment. A further embodiment allows for a user control to the control system 110 to manually select the mode (from a number of different modes of operation) such that the applied signal can be modified to suit different noise environments such as typically found in different care settings.

As already hinted, the sensing arrangement 420 described may be configured in an abundance of ways. It is unreasonable to present all possible configurations herein and it should be understood that the person skilled in the art will, after reading this disclosure, be able to configure the sensing system 420 in any way thinkable within the scope of the invention. For instance, the control unit 480 may be configured to configure the receiver 424 to detect disturbances in the sensor response signal S'. If disturbances are detected, the control unit may configure the sensing arrangement 420 to change e.g. carrier frequency fc of the carrier signal C, increase the power of the sensing signal S, change the mixing signal M etc. Such embodiments and any similar embroideries of the details presented herein are to be considered part of the inventive concept.

In one embodiment, the transmitter 423 is configured to transmit the carrier signal C without modulation for a first period of time and after the first period of time apply the mixing signal M to the carrier signal C for a second period of time. The first period of time being less than 50% of the second period of time, preferably less than 20% of the second period of time. This is beneficial since it enables the receiver 424 to detect the sensor response signal S' during the first period of time and then switch to more advanced detection techniques for the second period of time.

From the inventive concept of the sensing arrangement 420, it is clear that the sensing signal S may be time varying with regards to a frequency, an amplitude, modulation method, code and/or a phase of the sensing signal S. This may be accomplished by the mixing signal M, or the carrier signal C for that matter, being configured as e.g. a modulation signal, such that the mixing of the carrier signal S and the mixing signal M generates a sensing signal S with non-constant frequency, amplitude and/or a phase. This means that the carrier signal C and/or the modulation signal M will change its frequency, amplitude, modulation method, code and/or a phase over time.

In one embodiment the receiver 424 operates in a first mode of acquisition sensing until a change in the sensor response signal S' is detected at which point the receiver switches to a second detection sensing where the mixing response signal M' is analyzed. This may be implemented as a broad band power sensing of the sensor response signal S' in the acquisition sensing mode and when a change in signal power level is detected in the sensor response signal S', the mixing response signal M' sensor response signal S' is further analyzed. The acquisition sensing mode may be implemented by e.g. a simple power detector circuitry arranged to enable or wake up the receive mixer 428 when a power change is detected.

In some embodiments, the mixing signal M is a pulsed mixing signal M effectively implementing an on off keying, OOK, of the carrier signal C. These are preferred embodiments as the mixing signal M may be any suitable, preferably digital, signal that used to directly gate the carrier signal C. This embodiment is beneficial since it is implementable without the introduction of expensive RF-mixers, switching transistor or a relay may suffice depending on the speed of the mixing signal M, i.e. the modulation speed or mixing speed. Consequently, also the detection, i.e. the receiver 423, is simplified and the sensor response signal S' may be directly subjected to A/D conversion or using a simple timing analysis of the received signal compared to the transmitted signal.

The sampling speed of the A/D converter of the receiver 423 may be chosen such that the A/D itself has a mixing effect. As is known from e.g. the Nyquist sampling theorem, a sampling speed that is less than twice the highest frequency of the sampled signal will not accurately represent the sampled signal. In other words, if the carrier signal C is significantly higher than the modulation speed of the mixing signal M, the mixing signal may be acquired from the sensor response signal S' by sampling the sensor response signal S' at twice the modulation speed.

In one embodiment, the sensing signal S comprise a carrier frequency fc in the range of 80 kHz to 300 kHz. In other embodiments, the sensing signal S comprise a carrier frequency fc located within an Industrial, Scientific and Medical, ISM, frequency band.

In one embodiment, the sensing signal S comprise a mixing signal M with a constant variation. Such a mixing signal be a repetitive bit pattern such as an alternating bit pattern comparable to e.g. the preamble typically found in wireless communication. This is beneficial since it simplifies the detection, i.e. the receiver 423.

In one embodiment, a defined predefined or configurable proprietary bit pattern is used in mixing signal M to further allow identification of manufacturer or product type by creating a defined modulation response signal M' or carrier response signal C', i.e. generally a defined spectral response. The characteristic response of the identification component 390 will therefore be partly based on the applied stimulus using the proprietary bit pattern. As explained earlier with reference to FIG. 6*b*, each sequence of bits in the applied sensing signal S results in a different spectral response, i.e. differing amplitudes at various frequencies. The detection circuitry may be configured to specifically look for these. This is beneficial for e.g. a learning mode (detailed in coming sections) to provide a wider range of detection or for reducing the emitted noise or for increasing the immunity to external noise. The proprietary bit pattern may be very different in construction to previously described the bit patterns, e.g. the PRBS7 bit pattern. The proprietary bit pattern makes it possible for e.g. different manufacturer to choose differing sequences that allow for specific modulation response signals M' or carrier response signals C' associated with the n individual manufacturer or its specific product series. The proprietary bit pattern is advantageously combined with the previously disclosed embodiment wherein the identification device 390 is operated with a separate data storage device. The proprietary bit pattern may be provided to operate separate to or with the separate data storage device.

In one embodiment, the sensing signal S comprise a mixing signal M with a non-constant variation such as a pseudo random variation. A random mixing signal M will produce a flatter power spectrum with less risk of disturbing neighbouring equipment compared to a constant variation mixing signal M.

In one embodiment, the sensing arrangement 420 is a spread spectrum sensing arrangement, preferably as detailed with reference to FIG. 5.

In one embodiment, the control unit 480 is configured to control the sensing arrangement 420 according to a plurality of modes, each mode being associated with the sensing arrangement 420 emitting a distinguishable mixed radio frequency wave. That is to say, the sensing signal S may be configurable with regards to the carrier signal C, the mixing signal M, their respective frequencies $f_c$, $f_m$ or any combination thereof. In particular, in one embodiment, the carrier frequency $f_c$ is changed in a sweeping or a switching manner.

The switching of the carrier frequency $f_c$ may be performed according to a predetermined or configurable set of frequencies and be sequential in a decreasing, increasing, or seemingly random order. Each carrier frequency $f_c$ may be applied for a number of periods of the modulation signal M or for fractions of the period of the modulation signal. In the first case, the resulting mixing response signals M' are comparable to those illustrated in FIG. 6*b* where each delay would correspond to a different carrier frequency $f_c$. Alternatively or additionally, the mixing may be done with multiple generated and applied carrier frequencies $f_c$ in parallel, as a result the sensing signal S has even more frequency components compared to previous embodiments.

In one embodiment, the controller 480 is configured to compare the characteristic response, i.e. the sensor response signal S', the modulation response signal M' and/or the carrier response signal C', generated by the identification device 390 with a set of stored characteristic responses associated with a corresponding set of medical devices to identify the medical device 120. That is, the effect that the identification device 390 achieves in the operation of the sensor coil 425 for any given stimulus signal, is compared to a set of known responses, each associated with a medical device model or type.

In one embodiment, the control unit 480 is configured to control the controller device 110 based on the characteristic response generated by the identification device 390. That is, depending on what medical device 120 is sensed, the control unit 480 may send specific commands or data to the controller device to e.g. inform the controller device of a preferred or maximum allowed air pressure for a sensed medical device 120.

In one embodiment, the control unit 480 is configured to disable operation of the medical device 120 by means of the controller device 110 in response to the characteristic response generated by the identification device 390 being outside a predefined threshold range. That is, a malfunctioning, barred or obsolete medical device 120 may be identified by its identification device and use of the medical device 120 may be effectively disabled by the control unit 480.

In one embodiment, the sensor unit 421 comprises a transmitter 423 and a receiver 424. The transmitter 423 being configured to emit the mixed radio frequency waveform, the sensing signal S to the receiver 424 for forming a sensor field between said transmitter 423 and receiver 424. Typically, the sensor field is formed by the sensor coil 425 operatively connecting the receiver 424 to the transmitter 423.

As will be described hereinafter, a medical controller device arrangement and a medical device arrangement may be provided within the scope of the invention.

According to an aspect, a medical device arrangement for a medical device control system 100 is provided. The medical device arrangement may comprise a medical device 120 and a connector 330 in accordance with any one of the previously described embodiments connected to said medical device 120.

In one embodiment, the identification device 390 may be adapted to generate a characteristic response associated with the medical device 120.

In one embodiment, the identification device 390 may be adapted to generate at least one characteristic response associated with the medical device 120.

In a further embodiment, the identification device 390 may provide different characteristic responses to different applied stimulus to the sensing coil 425.

According to an aspect, a medical controller device arrangement is provided. The medical controller device arrangement is configured to be connected to a medical device 120 in a medical device control system 100 by means of a coupling assembly 300. The medical controller device arrangement comprises a controller device 110 for controlling the operation of a medical device 120. The coupling assembly 300 comprises a connector 330 connectable to a connecting member 310 for forming a connection through said connector 330 and connecting member 310.

The connecting member 310 is comprised in the medical controller device arrangement and the medical controller device arrangement further comprises a control unit 480 and a sensing arrangement 420 operatively connected to said control unit 480.

The sensing arrangement 420 is configured to emit a sensing signal (S) in the form of a mixed radio frequency waveform by mixing a carrier signal (C) and a mixing signal (M) for detecting a characteristic response associated with the medical device 120, said characteristic response being affected by an identification device 390 comprised in the connector 330 when energized by said sensing arrangement 420.

In one embodiment, the sensing arrangement 420 is configured to emit a time varying waveform.

In one embodiment, the sensing signal (S) has a carrier frequency ($f_c$) in the range of 80 kHz to 300 kHz.

In one embodiment, the mixing signal (M) is a pulsed signal such that the sensing signal (S) is a pulse modulated waveform.

In one embodiment, the mixing signal (M) has a constant variation. In one embodiment, the mixing signal (M) has a non-constant variation such as a pseudo random variation.

In one embodiment, wherein the sensing arrangement 420 is a spread spectrum sensing arrangement.

In one embodiment, the control unit 480 is configured to control the sensing arrangement 420 according to a plurality of modes, each mode being associated with the sensing arrangement 420 emitting a distinguishable sensing signal (S).

In one embodiment, the control unit 480 is configured to compare the one or at least one characteristic response generated by the identification device 390 with a set of stored characteristic responses associated with a corresponding set of medical devices to identify the medical device 120.

In one embodiment, the control unit 480 is configured to operate in a first learning mode where it is configured to obtain a characteristic response generated by an identification device 390 detected by means of the sensing arrangement 420 and update its prior set of stored characteristic responses based on said characteristic response detected by the sensing arrangement 420. Thus the control unit 480 is able to identify further medical devices 120 or medical controller devices 110 by means of operating in a learning mode wherein a newly detected characteristic response is added to the group of recognized medical devices 120 and/or medical controller devices 110.

In one embodiment, the control unit 480 is configured to operate in a second learning mode where it is configured to obtain at least one predefined characteristic response from an external source such that said at least one predefined characteristic response that was previously not part of the stored set of characteristic responses forms a part of the set of stored characteristic responses. For example, the result of this may be that a connected medical device 120 becomes operationally supported and can be used with the control system 100.

In one embodiment, the control unit 480 is configured to operate in an unlearning mode where it is configured to remove at least one of the prior set of stored characteristic responses such that the at least one characteristic response associated with the medical device 120 or the medical controller device 110 no longer forms part of the set of stored characteristic responses. For example, the result may be that the connected medical device 120 is no longer operationally supported and cannot be used with the control system.

The above mentioned learning and unlearning modes may be initiated in any suitable way e.g. from be initiated from a control panel of the medical device control system 100, via a device connected, directly or remotely, to the medical device control system 100 and/or via a communication command such as Bluetooth or WiFi.

In one embodiment, the medical controller device arrangement further comprises an indicating device 117 operatively connected to the control unit 480. The indicating device 117 may be configured to provide an indication to a user based on the characteristic response generated by the identification device 390.

In one embodiment, the control unit 480 is configured to control the controller device 110 based on the characteristic response generated by the identification device 390.

The control unit 480 may be configured to disable operation of the medical device 120 by means of the controller device 110 in response to the characteristic response generated by the identification device 390 being outside a predefined threshold range.

In one embodiment, the sensing arrangement 420 comprises at least one sensor unit 421.

In one embodiment, the sensor unit 421 comprises a transmitter 423 and a receiver 424, said transmitter 423 being configured to emit the sensing signal (S) to the receiver 424 for forming a sensor field between said transmitter 423 and receiver 424.

In one embodiment, the sensing arrangement 420 comprises a sensor coil 425 configured to couple the transmitter 423 and the receiver 424.

In one embodiment, the sensor coil 425 is provided on the connecting member 310.

In one embodiment, the sensor unit 421 is arranged externally from the connecting member 310.

According to an aspect, a medical device control system 100 comprising a medical device arrangement according to the aforementioned embodiments and a medical controller device arrangement according to the aforementioned embodiments is provided.

The invention has been described above in detail with reference to embodiments thereof. However, as is readily understood by those skilled in the art, other embodiments are equally possible within the scope of the present invention, as defined by the appended claims.

The invention claimed is:

1. A medical device control system comprising a medical device and a controller device configured to control the operation of the medical device, the medical device control system further comprising a coupling assembly for connecting the medical device and the controller device, wherein the coupling assembly comprises a connector and a connecting member, the connector being connectable to the connecting member, wherein the coupling assembly comprises an identification device, said identification device being adapted to generate a characteristic response associated with the controller device or the medical device, and wherein the medical device control system further comprises a control unit and a sensing arrangement operatively connected to said control unit, said sensing arrangement being configured to emit a sensing signal (S) in the form of a mixed radio frequency waveform by mixing a carrier signal (C) and a mixing signal (M) for detecting the characteristic response associated with the medical device or the controller device.

2. The medical device control system according to claim 1, wherein the sensing signal(S) is time varying with regards to a frequency, an amplitude and/or a phase.

3. The medical device control system according to claim 1, wherein the sensing signal(S) has a carrier frequency (fc) in the range of 80 KHz to 300 kHz.

4. The medical device control system according to claim 1, wherein the mixing signal (M) is a pulsed signal such that the sensing signal(S) is a pulse-modulated waveform.

5. The medical device control system according to claim 1, wherein the mixing signal (M) has a constant variation.

6. The medical device control system according to claim 1, wherein the mixing signal (M) has a non-constant variation.

7. The medical device control system according to claim 1, wherein the sensing arrangement is a spread spectrum sensing arrangement.

8. The medical device control system according to claim 1, wherein the control unit is configured to control the sensing arrangement according to a plurality of modes, each mode being associated with the sensing arrangement emitting a distinguishable sensing signal(S).

9. The medical device control system according to claim 1, wherein the control unit is configured to compare the characteristic response generated by the identification device with a set of stored characteristic responses associated with a corresponding set of medical devices or controller devices to identify the medical device or the controller device.

10. The medical device control system to claim 9, further comprising an indicating device operatively connected to the control unit, said indicating device being configured to provide an indication to a user based on the characteristic response generated by the identification device.

11. The medical device control system according to claim 1, wherein the control unit is comprised in the controller device and configured to control said controller device based on the characteristic response generated by the identification device.

12. The medical device control system according to claim 11, wherein the control unit is configured to disable operation of the medical device by means of the controller device in response to the characteristic response generated by the identification device being outside a predefined threshold range.

13. The medical device control system according to claim 12, wherein the sensing arrangement comprises at least one sensor unit.

* * * * *